United States Patent
Reinhard et al.

(10) Patent No.: US 6,280,418 B1
(45) Date of Patent: Aug. 28, 2001

(54) CONTAINER FOR STORING AND DISPENSING INJECTION, INFUSION AND DIAGNOSTIC PREPARATIONS

(75) Inventors: Michael Reinhard, Ober-Olm; Michael Spallek, Ingelheim, both of (DE)

(73) Assignee: Schott Glaswerke (DE)

( * ) Notice: Subject to any disclaimer, the term of this patent is extended or adjusted under 35 U.S.C. 154(b) by 0 days.

(21) Appl. No.: 08/921,665

(22) Filed: Sep. 2, 1997

Related U.S. Application Data

(63) Continuation of application No. 08/529,215, filed on Sep. 15, 1995, now abandoned.

(30) Foreign Application Priority Data

Sep. 28, 1994 (DE) ................................. 44 34 644

(51) Int. Cl.[7] .................................................. A61M 5/00
(52) U.S. Cl. ......................... 604/187; 604/19; 604/181; 604/187; 604/192
(58) Field of Search ............................ 604/19, 181, 187, 604/192, 199, 200, 218, 227, 236, 238, 240–243, 256, 257, 905, 263, 403

(56) References Cited

U.S. PATENT DOCUMENTS

| | | | |
|---|---|---|---|
| 2,711,171 | * 6/1955 | Dunnican | 604/241 |
| 3,055,363 | 9/1962 | Eckhart . | |
| 3,247,850 | 4/1966 | Gettig et al. . | |
| 3,524,445 | * 8/1970 | Frieze | 604/200 |
| 4,664,656 | * 5/1987 | Taddei | 604/241 |
| 4,781,701 | * 11/1988 | Geprags | 604/240 |
| 4,991,629 | * 2/1991 | Ernesto et al. | 604/256 |
| 5,125,415 | * 6/1992 | Bell | 604/403 |
| 5,125,892 | * 6/1992 | Drudik | 604/200 |
| 5,135,496 | * 8/1992 | Vetter et al. | 604/199 |
| 5,468,232 | * 11/1995 | Naganuma | 604/200 |
| 5,554,125 | * 9/1996 | Reynolds | 604/200 |
| 5,554,134 | * 9/1996 | Bonnichsen | 604/240 |

FOREIGN PATENT DOCUMENTS

| | | |
|---|---|---|
| 19 66 623 | 8/1973 | (DE) . |
| 3916101 | 11/1990 | (DE) . |
| 0519240 | 12/1992 | (EP) . |
| 0 567 186 A1 | 10/1993 | (EP) . |
| 2 249 727 | 5/1992 | (GB) . |
| WO 9000073 | 1/1990 | (WO) . |
| WO 9204927 | 4/1992 | (WO) . |

\* cited by examiner

*Primary Examiner*—Glenn K. Dawson
(74) *Attorney, Agent, or Firm*—Kilpatrick Stockton LLP

(57) ABSTRACT

The invention concerns a container for injection, infusion, and diagnostic preparations, serving, on the one hand, as a long-term storage container, and, on the other, as a device for directly dispensing the preparations. The container has a glass barrel with a glass headpiece with a connector cone that acts as a nozzle. This is molded onto a glass barrel, thereby forming a single unit. A separate plastic, threaded section of an interlocking, conical joint is mounted onto the connector cone, accommodating a secured sealing cap that can be removed from the connector cone. The other opening of the glass barrel is sealed by a plunger that has a connection spot for a plunger rod. Furthermore, the container has a plastic grip mounted onto the inner wall of the glass barrel. Since the container, including the external profile, is, on the whole, designed to resemble a standard syringe, it ensures that the invented container can be accommodated by all current syringe pumps.

5 Claims, 4 Drawing Sheets

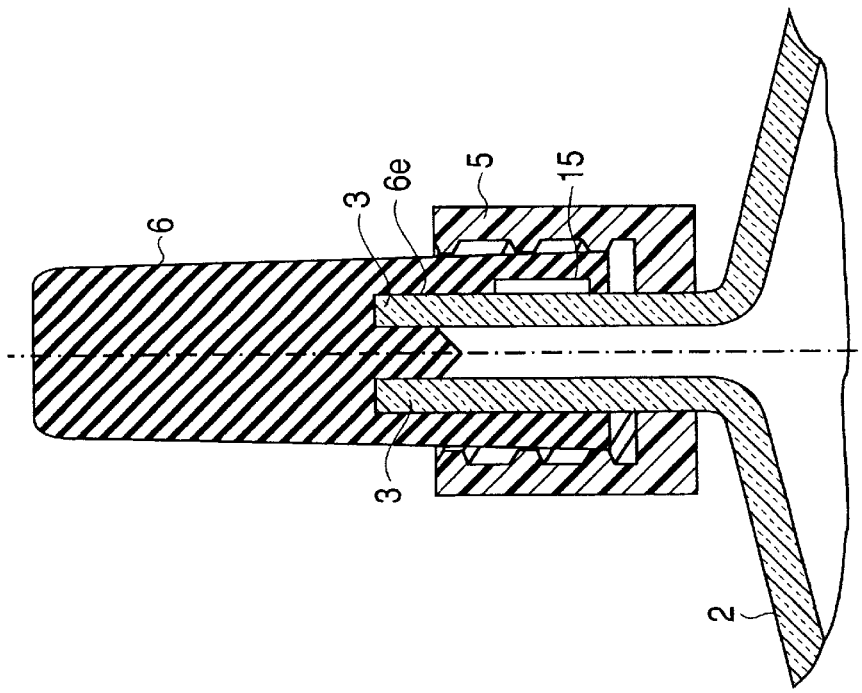
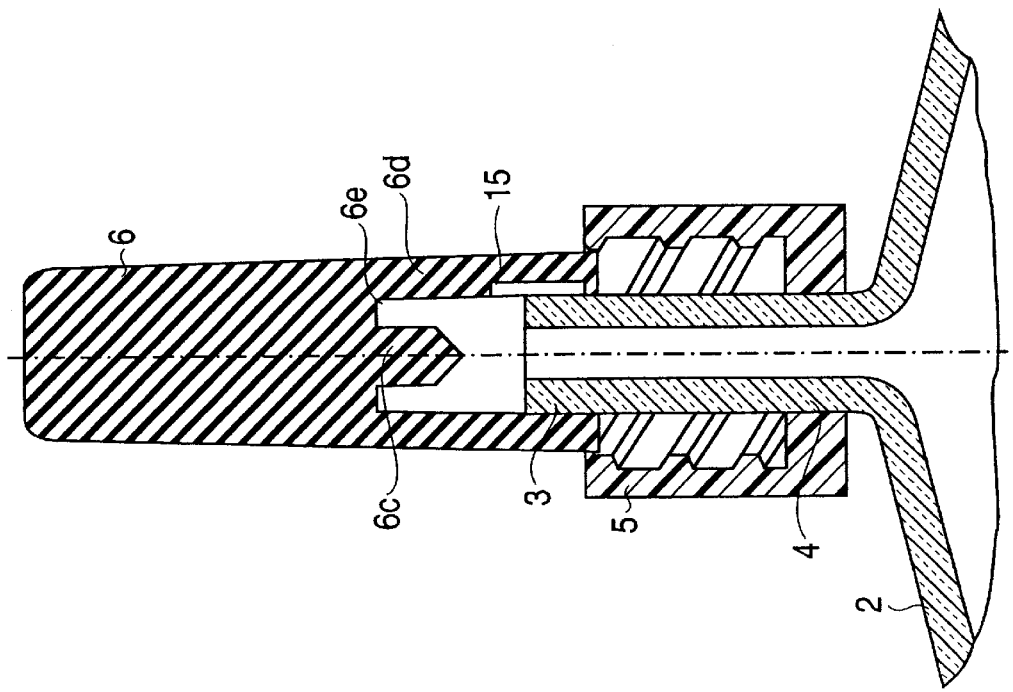

CONTAINER FOR STORING AND DISPENSING INJECTION, INFUSION AND DIAGNOSTIC PREPARATIONS

This application is a continuation of application Ser. No. 08/529,215, filed Sep. 15, 1995 now abandoned.

BACKGROUND OF THE INVENTION

1. Field of the Invention

The present invention relates generally to a container to be used for long-term storage, as well as for direct dispensing of injection, infusion, and diagnostic preparations, having fill volumes in the range of 10 to 200 ml. In particular, the invention relates to a storing and dispensing container comprising a glass barrel having, on a top end, a sealed portion that can be opened for dispensing into a hollow needle or infusion tube, and having, on a base end, a grip, a stopper that serves as a plunger, and a connection point where a supporting plunger rod can be connected.

2. Description of the Prior Art

For the purpose of dispensing injection, infusion, and diagnostic preparations, glass containers for storing the preparations are distributed as fully filled and sealed with a rubber stopper. This rubber stopper is formed in such a way as to be self-sealing when repeatedly pierced by a syringe needle, particularly by one of the plastic, disposable syringes now in common use This allows the needle to be drawn repeatedly from the storage container.

It is also known that the aforementioned storage containers can be made, or rather equipped with additional components, in such a way that they can retain the function of syringes, and their respective preparations can be dispensed directly from the container itself. This eliminates the need for transferring from a container to a now standard plastic syringe, significantly reducing the energy expended and the risks of confusing and contaminating the preparations. In addition, when considering the total cost of drug delivery, administering preparations directly from the container represents by far the most economical possibility.

Such a container is known from European Patent No. 0,298,585 A1, having a fill volume between 20 and 100 ml and is in principle a vial with a variable bottom. With a total height to diameter ratio of no more than 2.5:1, this container corresponds to typical injection vials that have analogous dimensions of less than 2.9:1. In place of a glass bottom, this vial has a rubber stopper to which a plunger rod can be mounted. Similarly, section 1, the mouth of the vial is designed as a flared flange, sealed with a rubber stopper similar to DIN ISO 8362, section 2, and has an aluminum flange cap, to secure the rubber stopper in its position.

To activate, the center area of the rubber stopper must be accessible. For flange caps that do not have an existing center opening, but are instead sealed, the center area is first removed. For this, an opening mechanism with a preset breaking point is provided. Then, in the next step, the exposed area of the rubber stopper must be disinfected, followed by the actual activation of the vial by placing an activating fixture over the flange cap. The activating fixture is equipped with a needle that is centered on the side facing the rubber stopper such that the rubber is pierced when the fixture is put into place, providing access to the preparation. For injection purposes, the needle can be two sided, i.e., the one side serves to puncture the rubber for activation, while the other, longer side of the needle functions as a hypodermic needle. For other purposes, the activation fixture is only provided with the needle on the one side, while the other side is designed as an interlocking, conical joint. A hollow needle or, alternatively, an infusion tube can be connected to this joint.

The disadvantage to this familiar container is that only once the activation fixture is in place does the function of the variable bottom vial become that of a syringe. The dimensions of this syringe, however, have a total height to outer diameter ratio of no more than 2.5:1, making the syringe unusable for common syringe pumps, as these are envisioned for the non-filled, disposable, plastic syringes currently on the market.

Being able to insert the syringe into a syringe pump is nevertheless a significant demand, as the preparation in many medicinal applications is dispensed by means of a syringe pump, into which a syringe is inserted. The supporting plunger is moved by an adjustable feed, while the body of the syringe is fixed, thus expelling the preparation into an infusion tube. In practice, forces of over 50 N can be applied to the syringe grip, and so the grip of any syringe suitable for syringe pumps must be able to withstand tractive forces significantly higher than 50 N.

An overview of typical syringe pumps currently on the market is given in the American Journal of Hospital Pharmacy, Vol. 48, October 1991, Suppl. 1, pp. S36–S51 (publisher, American Society of Hospital Pharmacists, Inc.).

A further disadvantage of this known container system lies in the need for an activating fixture in addition to the container. Cleaning the rubber stopper in the area where the activating needle pierces the stopper, as well as where the activating fixture is placed, requires a significant amount of handling.

Furthermore, rubber stoppers must always be punctured, possibly producing tiny rubber particles, which can be problematic from a medical point of view.

A further disadvantage of the known system lies in the necessary use of aluminum flange caps, which, on the one hand, produce abrasive particles during the filling process and, on the other hand, complicate recycling and separation of materials in non-pharmaceutical areas.

Yet another barrel that can be packaged with a syringe is known from German Patent No. DE 3,924,830 A1. This barrel consists of a glass pipe having, on one end, a retractable plunger rod with finger support and, on the cannula, a locking component in the form of a pierceable rubber stopper with headpiece. This syringe barrel is noted for its complicated design and numerous pieces; when using the syringe, rubber components must be punctured, leading to the disadvantages explained earlier. Inclusion of a finger support and headpiece increases the diameter of the syringe barrel to wider ranges, thereby having the disadvantage of making impossible the use of such syringes in syringe pumps. The same is true of the analogously built syringes found in German Patent No. DE 3,916,101 A1 and PCT Patent Publication No. WO 91/01152.

SUMMARY OF THE INVENTION

The task underlying this invention is to create a container of the type described in the introduction, which requires a minimum amount of handling when dispensing the preparation, allows for dispensing with typical syringe pumps currently on the market, does not require any rubber parts to be punctured, contains no metal components, and is particularly economical to manufacture.

The solution to this task is achieved in the present invention by:

converting the dimensions of the container, with respect to the total height to outer diameter ratio, to the dimensions of a standard syringe (ratio is larger than 2.5:1), molding a tapered glass headpiece onto the glass barrel, thereby forming a single unit with a connector cone at the top end that serves as a nozzle, attaching a separate, threaded section of a plastic, interlocking, conical joint concentric to the connector cone, designing the threaded section to accommodate a sealing cap that serves as a stopper and can be sealed via the connector cone, and mounting a plastic grip, which can withstand a tractive force of at least 100 N, onto the interior wall of the glass barrel.

This design has the advantage that, when dispensing the preparation, an infusion tube or needle can be immediately attached after the simple process of removing the sealing cap. Another particularly important feature is that a plastic grip is mounted on the inside of the syringe barrel. In this way, the grip and barrel can be designed in such a way that the exterior contour of the container—even in the transition area from the grip to the syringe barrel—is identical to the exterior contour of plastic syringes now used in syringe pumps. This guarantees that the container of the present invention can be accommodated by all current syringe pumps. In addition, the small number of parts makes it possible to manufacture the syringes economically.

Glass barrels for hypodermic syringes, having a fill volume in the range of 0.5–10 ml and a molded glass finger support, are known from DIN 58358, section 4.

Furthermore, so-called prefilled, finished glass syringes with a smaller fill volume range (20 ml) are known from European Patent No. EP 0,382,126 A2. Here, the syringe barrel and nozzle area, not including the interlocking, conical joint, are made of glass, as is the grip, which is directly molded onto the barrel. Syringes found in U.S. Pat. No. 3,865,236 and German Patent No. DE 2,339,180 are designed in a similar fashion. These syringes are used primarily for injections. For special uses, there are also finished glass syringes with an interlocking, conical joint fastened concentrically to the connector cone.

Due to their design, however, these syringes are not suitable for use in a standard syringe pump.

In one development of this invention, the connector cone has a groove on its conical, outer lateral surface, in an area lying more than 5 mm from its tip—this is where the separate, threaded section of the interlocking, conical joint is inserted by way of a form-fitting, snap connection. This has the advantage of offering a high degree of security against any loosening of the connection, in that the loose, threaded section of the plastic, interlocking, conical joint is snapped into a groove.

In another design in which the nozzle has a groove in the transition area between the connector cone and syringe barrel, i.e., with a larger groove diameter, the stability of the bond to the interlocking, conical joint is improved, while, at the same time, the mechanical strength of the container at the mouth of the connector cone is increased.

In place of the bonding of the separate, threaded piece by means of a snap connection, the threaded piece can, in both of the aforementioned designs, be glued to the connector cone, that is, in the transition area with the syringe barrel. This type of container has the advantage of eliminating the need to make a groove on a glass surface.

There are a number of options available for accommodating the sealing cap in the separate, threaded piece. In the simplest case, the cap has an exterior thread and can be screwed into the threaded piece, which possesses an interior thread. The cap, then, has an elastic lining or insert that seals onto the conical, exterior lateral surface and/or face of the connector cone.

A small axial enlargement in the cap area is obtained when, after further development of the invention, a lid-like cap with an interior thread can be screwed onto the separate, threaded section of the plastic, interlocking, conical joint, which possesses an exterior thread. The cap then has an elastic lining or insert that seals onto the conical, exterior lateral surface and/or face of the connector cone.

A further possibility for fastening the sealing cap in an economical and easy-to-handle manner is to make the sealing cap out of rubber, with an interior contour corresponding to the exterior contour of the connector cone, whereby the diameter of the interior contour of the sealing cap is undersized with respect to the exterior contour of the connector cone. The sealing cap is then put or twisted into place on the connector cone, sealing the interior lateral surface of the cap onto the conical, exterior lateral surface of the connector cone.

When filling the syringe, a significant advantage is obtained if the container in this invention is further developed in such a way that the smallest interior diameter of the separate, threaded section of the interlocking, conical joint, including the snap portion or glue surface, is larger than the largest exterior diameter of the sealing cap. The top section of the syringe is first sealed by pressing the cap firmly onto the connector cone. The smallest interior diameter of the interlocking, conical joint is so large that it can be brought over the sealing cap and fastened in the groove or glue spot afterwards. This means that the interlocking, conical joint does not have to be brought into the sterile area when filling under antiseptic conditions, offering a substantial advantage in handling and cost.

One feature of the invention under development is an interlocking, conical joint equipped with a safety cap with a preset breaking point. In this way, two objectives are pursued: on the one hand, the safety cap serves to protect against accidental removal or loosening of the sealing cap, and on the other hand, it also demonstrates a unique connection.

The special design of a sealing cap having, in the sleeve area, one or more axial grooves on its interior surface, facilitates lyophilization in the syringe when the cap is already in place. The sealing cap is first pressed firmly onto the connector cone to obtain a sealing effect. The syringe is then filled via the open cylindrical end of the barrel, with the connector cone and sealing cap now located underneath. After filling, the plunger head is put into place, the syringe is rotated, and the sealing cap is lifted to the point where, on the one hand, it is still resting firmly on the connector cone, yet, on the other hand, contact is established between the interior of the syringe and the environment via the axial grooves on the interior surface of the lower portion of the cap sleeve. Lyophilization can now take place, and, by firmly pressing the sealing cap completely back into place, the container can still be fully sealed within the lyophilizer.

Further features under development and advantages of this invention are given by means of the sample designs presented in the drawings.

BRIEF DESCRIPTION OF THE DRAWINGS

FIGS. 4a and 4b show longitudinal section views of a fourth embodiment of the container nozzle of FIG. 1; in particular, FIG. 4a shows a container opened for lyophilization, and FIG. 4b shows a closed container.

DETAILED DESCRIPTION OF THE PREFERRED EMBODIMENTS

Figure 1:
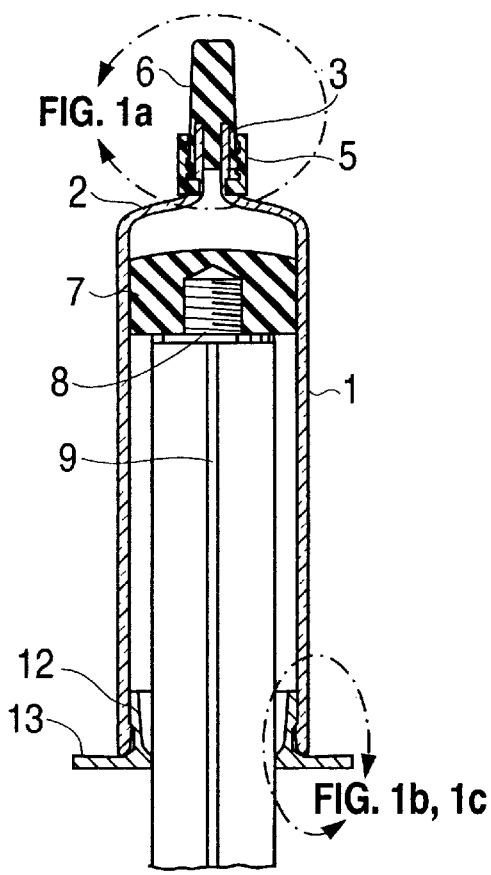
FIG. 1 shows a longitudinal section of the container according to a first embodiment of the present invention.
Figure 1A:
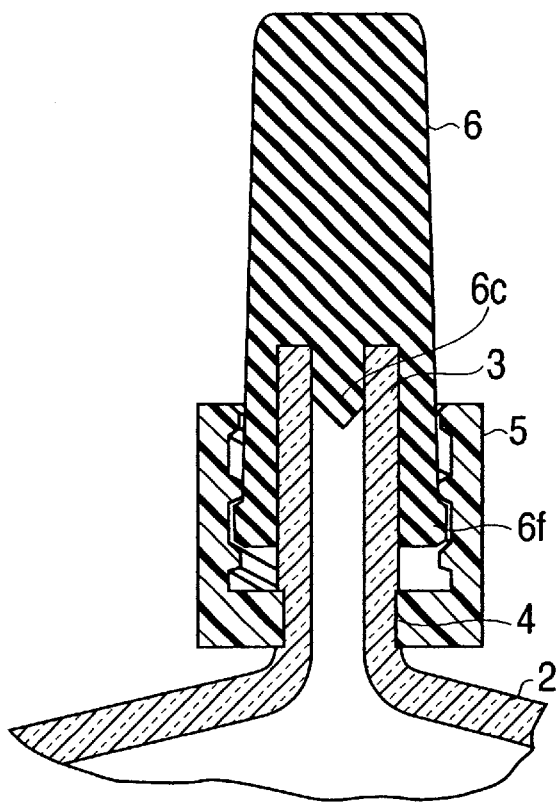
FIGS. 1a and 1b show detailed enlargements of portions of the container shown in FIG. 1.
Figure 1B:
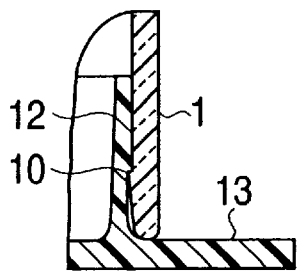
Figure 1C:
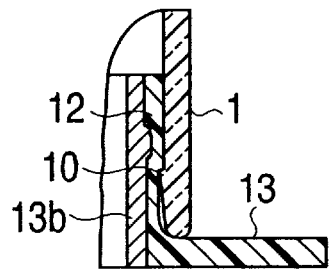
FIG. 1c shows a modified version of FIG. 1b in which a safety collar has been inserted.
Figure 1D:
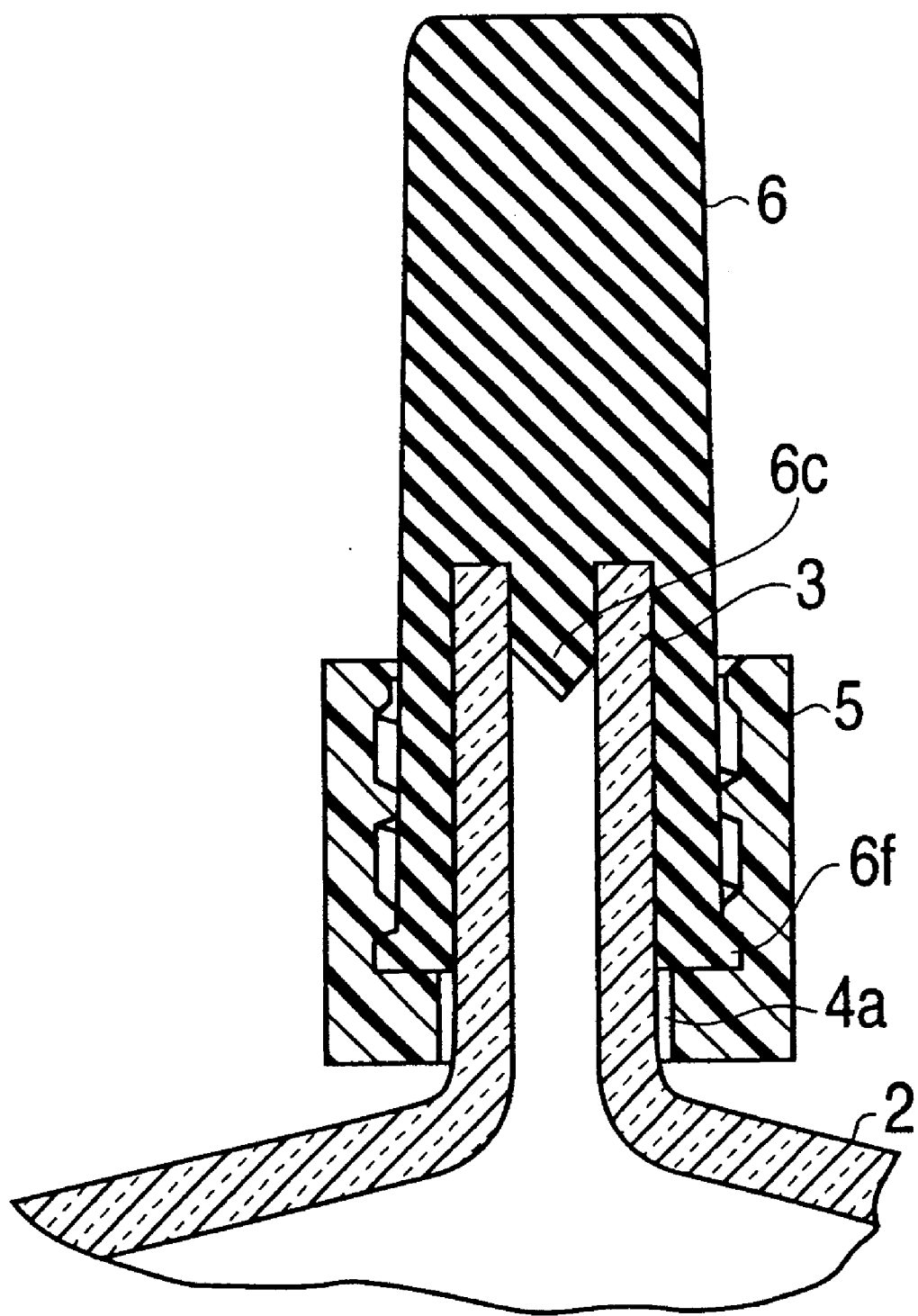
FIG. 1d shows a modified version of FIG. 1a in which adhesive is used to attach the collar to connecting cone.

FIG. 1–1d show various aspects of a container according to the present invention for storage, as well as direct dispensing, of injection, infusion and diagnostic preparations, having fill volumes in the range of 10 to 200 ml. The container is manufactured as a syringe, whereby FIG. 1 shows the syringe in a closed state. The dimensions of the container, with respect to the total height to outer diameter ratio, are therefore adjusted to those of a standard syringe, i.e., the ratio is larger than 2.5:1.

The container consists of a glass cylinder (1), a syringe barrel, which has a tapered glass top section (2) with a glass connector cone (3), and a nozzle molded onto its top end, forming a single unit. This can be seen especially well in the detailed enlargement in FIG. 1a. The connector cone (3) has a groove (slot) (4), into which a separate, threaded portion of a plastic, interlocking, conical joint is inserted concentrically around the connector cone by twisting, creating a form-fitting snap connection. The threaded piece (5) accommodates a sealing cap (6), preferably a rubber cap, by means of which the connector cone (3) can be tightly sealed or locked by twisting the threaded piece (5), forming a conical joint to the cap (6). The inner contour of the sealing cap (6) has a profile corresponding to the exterior contour of the connector cone (3), but is nevertheless undersized with respect to the diameter of the connector cone (3). After the sealing cap has been firmly pressed or twisted onto the connector cone (3), the interior lateral surface of the sealing cap forms a seal with the conical, exterior lateral surface of the connector cone. Furthermore, the sealing cap has a lining (6c) made of an elastic material, which forms a seal with the face and the conical, exterior lateral surface of the connector cone (3).

During fitting of the sealing cap (6), the cap is screwed into the threaded piece. Subsequently the threaded piece (5) via an external fitting (6f) of the cap (6) (5), the sealing cap (6) can be removed, and a hypodermic needle or infusion tube (both not shown)—depending on the application purpose, i.e., dispensing method—can be attached to the glass connector cone (3) and locked by means of the loose threaded piece (5), forming a conical joint.

The groove (4) is placed far enough from the front rim of the loose threaded piece (5) that the rubber cap (6) and later the hypodermic needle or infusion tube can be pressed sufficiently far onto the connector cone (3). The distance between the groove and the tip of the connector cone should be greater than 5 mm.

The opposite end of the glass cylinder (1) from the nozzle is sealed by a piston (or stopper) (7), preferably made of rubber. A piston rod (or plunger) (9) can be fastened to the piston (or stopper) by way of a (preferably) threaded connector point (8). At its open end, the interior of the syringe barrel is equipped with an undercut (10), in which the lip of a cylindrical extension (12) of a grip (13) snaps into place. This can be seen especially well in FIG. 1b. FIG. 1c shows a special design for securely fastening the grip (13)—here the grip snaps into a safety collar (13b), which has been inserted to ensure that the grip cannot be pulled out.

Once the sealing cap (6) is in place and the piston rod (9) has been removed, leaving the piston (or stopper) (7) at the open end of the glass cylinder (1), as well as the lip of the syringe, the invented container provides for the long-term storage of the prefilled preparation. With this container, however, even when manufactured as a syringe (FIG. 1), the preparation can be delivered directly to the patient by removing the sealing cap (6), and replacing it with a needle or infusion tube. The piston (or stopper) then forces the preparation out of the container and into the needle or infusion tube, whereby the shape of the container is designed in such a way as to allow for the use of a syringe pump—a significant advantage for infusion and diagnostic purposes.

Figure 2:
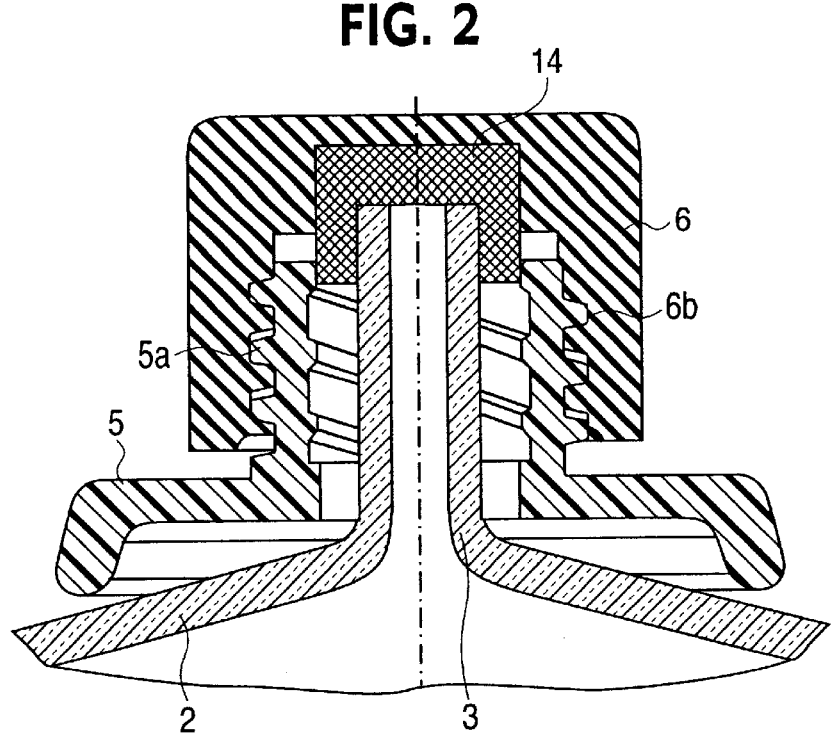
FIG. 2 shows a longitudinal section of a second embodiment of the container nozzle of FIG. 1.

FIG. 2 shows a second design for the nozzle of the invented container, which can be distinguished from the nozzle in FIG. 1 by the design of the sealing cap. The cap (6) shown in FIG. 2 is provided with an interior thread (6b) and is screwed onto the separate, threaded section (5) of the interlocking, conical joint (Luer Lock fastening), which has the corresponding external thread (5a). A rubber insert (14) is placed in the center of the sealing cap (6), forming a seal with the face and lateral surface of the connector cone. Otherwise, the design in FIG. 2 corresponds to that of FIG. 1, which is underscored by the uniformity of reference numerals for equivalent components.

Figure 3:
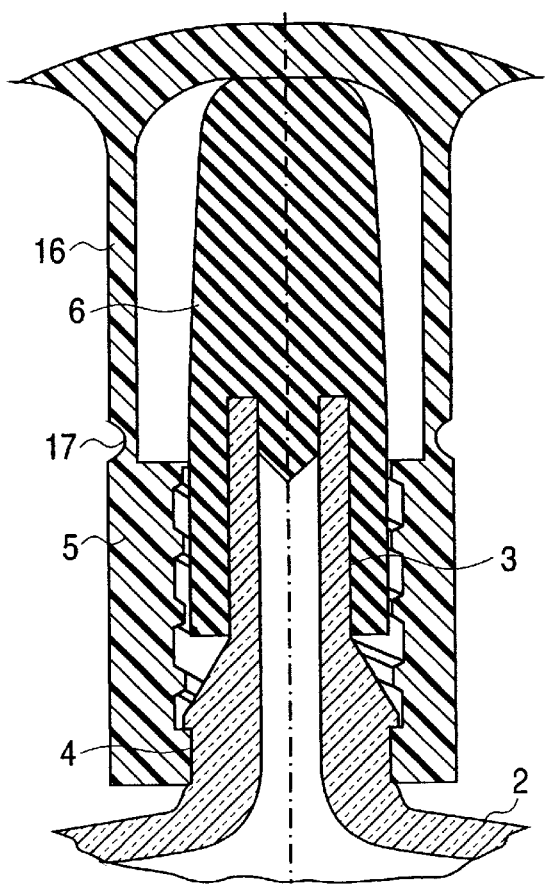
FIG. 3 shows a longitudinal section of a third embodiment of the container nozzle of FIG. 1.
Figure 3A:
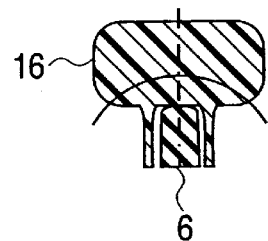
FIG. 3a shows a detailed cross-section of the top portion of the safety cap shown in FIG. 3.

FIG. 3 shows yet another special design based on the nozzle in FIG. 1. The threaded section (5) of the interlocking, conical joint snaps into a groove (4) located in the transition area (2) between the syringe barrel and the connector cone (3). The safety cap (16), surrounding the sealing cap (6), is connected to the threaded section of the interlocking, conical joint via a set breaking point (17). The safety cap (16) is equipped in such a way as to prevent the sealing cap (6) from being accidentally removed. To simplify opening, the safety cap (16) is equipped with the profiling shown. The design of the top portion of the safety cap (16) is shown in FIG. 3a in more detail, with the curved line corresponding to the upper profile (cut-off line) of FIG. 3. Other designs are conceivable. The grip feature is significant in the design.

The smallest inner diameter of the separate, threaded section (5) of the interlocking, conical joint, including that of the snap connection, is larger than the largest outer diameter of the sealing cap (6). This also allows the safety cap (16) along with the separate, threaded piece to be mounted once the sealing cap has been put in place.

FIGS. 4a and 4b show an analogous nozzle to that in FIG. 1, yet with the difference that the sealing cap (6) has one or more grooves (15) running axially on the interior surface of the lower portion of the cap sleeve (6d).

FIG. 4a shows the opened sealing cap (6) on the connector cone (3). The principle characteristic of the open state is that the cap (6) has not been completely pressed down onto the connector cone (3), guaranteeing contact between the interior of the syringe and the environment via the groove (15), so that the syringe can be lyophilized. FIG. 4b shows the closed position. After lyophilization, the sealing cap (6)

is pressed down completely on the connector cone (3), so that the interior, closed conical surface (6e) forms a seal with the connector cone (3).

What is claimed is:

1. A container to be used for injection, infusion, and diagnostic preparations having a filling volume ranging from 10 to 200 ml for long-term storage and for direct dispensing of the preparations, the container comprising:

a glass cylinder; and a converging glass headpiece molded to the glass cylinder as one piece, the converging glass headpiece having a stopper-less connecting cone;

wherein the container has dimensions in which the ratio of total height to outer diameter of the container is greater than 2.5:1;

wherein a separate threaded coupling is attached concentrically to the stopper-less connecting cone;

wherein the threaded coupling is adapted to receive a sealing cap as a closing element:

wherein, when the connecting cone is tightly closed, the sealing cap is removable for direct injection, such that the threaded coupling may receive at least one element selected from the group consisting of a needle and an infusion line;

wherein the glass cylinder has an inside wall and is connected to a foot portion, the foot portion having a finger grip, wherein the finger grip has a cylindrical extension that is attached to the inside wall of the glass cylinder;

wherein the glass cylinder is capable of receiving a stopper, the stopper serving as a piston and the stopper including a connecting point for attaching a piston rod;

wherein the connecting cone includes an exterior surface converging toward a tip;

wherein the connecting cone comprises a groove, located more than 5 mm from the tip;

wherein the exterior surface of the connecting cone has a predetermined outer diameter in the area adjacent the groove; and wherein the threaded coupling includes a radially inward extending portion, the radially inward extending portion having a radially inner diameter, and the radially inner diameter of the inward extending portion being less than the predetermined outer diameter of the exterior surface, such that the radially inward extending portion of the threaded coupling can be snap fit into the groove to connect the threaded coupling to the glass cylinder.

2. A container to be used for injection, infusion, and diagnostic preparations having a filling volume ranging from 10 to 200 ml for long-term storage and for direct dispensing of the preparations, the container comprising:

a glass cylinder; and a converging glass headpiece molded to the glass cylinder as one piece, the converging glass headpiece having a stopper-less connecting cone;

wherein the container has dimensions in which the ratio of total height to outer diameter of the container is greater than 2.5:1;

wherein a separate threaded coupling is attached concentrically to the stopper-less connecting cone;

wherein the threaded coupling is adapted to receive a sealing cap as a closing element;

wherein, when the connecting cone is tightly closed, the sealing cap is removable for direct injection, such that the threaded coupling may receive at least one element selected from the group consisting of a needle and an infusion line;

wherein the glass cylinder has an inside wall and is connected to a foot portion, the foot portion having a finger grip, wherein the finger grip has a cylindrical extension that is attached to the inside wall of the glass cylinder;

wherein the glass cylinder is capable of receiving a stopper, the stopper serving as a piston and the stopper including a connecting point for attaching a piston rod;

wherein the threaded coupling is snap fit into a groove located on the connecting cone.

3. A container to be used for injection, infusion, and diagnostic preparations having a filling volume ranging from 10 to 200 ml for long-term storage and for direct dispensing of the preparations, the container comprising:

a glass cylinder; and a converging glass headpiece molded to the glass cylinder as one piece, the converging glass headpiece having a stopper-less connecting cone;

wherein the container has dimensions in which the ratio of total height to outer diameter of the container is greater than 2.5:1;

wherein a separate threaded coupling is attached concentrically to the stopper-less connecting cone;

wherein the threaded coupling is adapted to receive a sealing cap as a closing element;

wherein, when the connecting cone is tightly closed, the sealing cap is removable for direct injection, such that the threaded coupling may receive at least one element selected from the group consisting of a needle and an infusion line;

wherein the glass cylinder has an inside wall and is connected to a foot portion, the foot portion having a finger grip, wherein the finger grip has a cylindrical extension that is attached to the inside wall of the glass cylinder;

wherein the glass cylinder is capable of receiving a stopper, the stopper serving as a piston and the stopper including a connecting point for attaching a piston rod;

wherein the connecting cone has a tip; further comprising an internal thread on the threaded coupling into which the sealing cap can be screwed, the sealing cap having an external thread and at least one element selected from the group consisting of a lining and an insert, the at least one element selected comprising an elastic material that forms a seal with the tip of the connecting cone.

4. A container to be used for injection, infusion, and diagnostic preparations having a filling volume ranging from 10 to 200 ml for long-term storage and for direct dispensing of the preparations, the container comprising:

a glass cylinder; and a converging glass headpiece molded to the glass cylinder as one piece, the converging glass headpiece having a stopper-less connecting cone;

wherein the container has dimensions in which the ratio of total height to outer diameter of the container is greater than 2.5:1;

wherein a separate threaded coupling is attached concentrically to the stopper-less connecting cone;

wherein the threaded coupling is adapted to receive a sealing cap as a closing element;

wherein, when the connecting cone is tightly closed, the sealing cap is removable for direct injection, such that the threaded coupling may receive at least one element selected from the group consisting of a needle and an infusion line;

wherein the glass cylinder has an inside wall and is connected to a foot portion, the foot portion having a finger grip, wherein the finger grip has a cylindrical extension that is attached to the inside wall of the glass cylinder;

wherein the glass cylinder is capable of receiving a stopper, the stopper serving as a piston and the stopper including a connecting point for attaching a piston rod;

wherein the connecting cone has an exterior contour and the sealing cap is made of an elastic material; wherein the sealing cap has an interior contour having a profile that corresponds to the exterior contour of the connecting cone; and wherein the interior contour of the sealing cap is undersized with respect to the exterior contour of the connecting cone, such that the sealing cap may be firmly pressed or twisted onto the connecting cone, the sealing cap thereby forming a seal with the connecting cone.

5. A container to be used for injection, infusion, and diagnostic preparations having a filling volume ranging from 10 to 200 ml for long-term storage and for direct dispensing of the preparations, the container comprising:

a glass cylinder; and a converging glass headpiece molded to the glass cylinder as one piece, the converging glass headpiece having a stopper-less connecting cone;

wherein the container has dimensions in which the ratio of total height to outer diameter of the container is greater than 2.5:1;

wherein a separate threaded coupling is attached concentrically to the stopper-less connecting cone;

wherein the threaded coupling is adapted to receive a sealing cap as a closing element;

wherein, when the connecting cone is tightly closed, the sealing cap is removable for direct injection, such that the threaded coupling may receive at least one element selected from the group consisting of a needle and an infusion line;

wherein the glass cylinder has an inside wall and is connected to a foot portion, the foot portion having a finger grip, wherein the finger grip has a cylindrical extension that is attached to the inside wall of the glass cylinder;

wherein the glass cylinder is capable of receiving a stopper, the stopper serving as a piston and the stopper including a connecting point for attaching a piston rod;

further including a safety collar within the cylindrical extension of the finger grip, the safety collar being held within the cylindrical extension by a snap connection.

* * * * *